United States Patent [19]

Courty et al.

[11] 4,199,437

[45] Apr. 22, 1980

[54] PROCESS FOR STEAM DEALKYLATION OF AROMATIC HYDROCARBONS

[75] Inventors: Philippe Courty, Houilles; Jean-François Le Page; André Sugier, both of Rueil Malmaison; Jean Cosyns, Maule, all of France

[73] Assignee: Institut Francais du Petrole, Rueil Malmaison, France

[21] Appl. No.: 14,400

[22] Filed: Feb. 23, 1979

[30] Foreign Application Priority Data

Feb. 24, 1978 [FR] France ............................. 78 05367

[51] Int. Cl.$^2$ .................. B01J 23/64; C07C 3/58; C07C 15/06; C10G 35/08

[52] U.S. Cl. .................................. 208/124; 208/62; 208/112; 208/138; 252/466 PT; 423/652; 585/487

[58] Field of Search ............... 208/112, 124, 138, 62; 252/466 PT; 423/652; 585/487

[56] References Cited

U.S. PATENT DOCUMENTS

| | | | |
|---|---|---|---|
| 3,436,433 | 4/1969 | Lester | 585/487 |
| 3,530,194 | 9/1970 | Quik et al. | 208/111 X |
| 3,551,326 | 12/1970 | Egan | 208/112 X |
| 3,595,932 | 7/1971 | Maslyanski et al. | 585/487 |
| 3,617,520 | 11/1971 | Kluksdahl | 208/138 |
| 3,649,706 | 3/1972 | Lester | 208/74 X |
| 3,649,707 | 3/1972 | Lester | 585/487 |
| 3,650,944 | 3/1972 | McCoy et al. | 208/65 |
| 3,670,044 | 6/1972 | Drehman et al. | 208/138 X |
| 3,819,507 | 6/1974 | Oishi | 208/139 |
| 4,013,734 | 3/1977 | Kim | 585/487 |

FOREIGN PATENT DOCUMENTS

| | | | |
|---|---|---|---|
| Ad.92077 | 8/1968 | France | 208/124 |
| 1588876 | 4/1970 | France | 208/124 |
| 2317962 | 2/1977 | France | 208/124 |
| 213776 | 2/1971 | U.S.S.R. | 208/124 |
| 236469 | 2/1971 | U.S.S.R. | 208/124 |

*Primary Examiner*—Delbert E. Gantz
*Assistant Examiner*—G. E. Schmitkons
*Attorney, Agent, or Firm*—Millen & White

[57] ABSTRACT

Process for steam dealkylation of alkylaromatic hydrocarbons, particularly useful to produce benzene from toluene and to de-alkylate the alkylaromatic hydrocarbons contained in the effluents from catalytic reforming and aromatic production units, wherein the catalyst contains, in addition to an alumina carrier (a) at least one metal selected from ruthenium, rhodium, palladium, osmium, iridium and platinum (b) rhenium and (c) an alkali metal selected from lithium, sodium, potassium, rubidium and cesium.

7 Claims, 2 Drawing Figures

PROCESS FOR STEAM DEALKYLATION OF AROMATIC HYDROCARBONS

BACKGROUND OF THE INVENTION

This invention concerns steam dealkylation reactions for producing benzene or the lower homologs thereof by dealkylation of toluene and of other alkylbenzenes.

Many catalysts have been proposed for the steam dealkylation of aromatic hydrocarbons, said catalysts containing a porous carrier and at least one metal deposited on the carrier. By way of examples, there can be mentioned:

U.S.S.R. Pat. No. 213,776, wherein the catalyst contains rhodium, nickel and alumina;

U.S. Pat. No. 3,595,932, wherein the catalyst contains a noble metal of the platinum family (platinum, palladium, rhodium, iridium, ruthenium) deposited on a carrier consisting of alumina or a combination of alumina with nickel or cobalt;

U.S. Pat. No. 3,436,433, wherein the catalyst contains alumina an alkaly metal, ferric oxide, rhodium and chrominum;

U.S. Pat. No. 3,649,706 and 3,649,707, wherein the catalysts contain mixtures of an alkali metal, ferric oxide, chromium and a metal selected from platinum, palladium and rhodium;

U.S. Pat. No. 4,013,734, wherein the catalyst contains alumina, a noble metal of the platinum family and a metal selected from vanadium, niobium and tantalum; and French Pat. No. 2,317,962, wherein the catalyst contains alumina or aluminasilicates as well as rhodium and a metal from group IV A, particularly tin.

The catalysts used up to now exhibit rather good performances with respect to activity, but, on the one hand, their stability is insufficient; and, on the other hand, their selectivity is not sufficiently high; as a matter of fact, in addition to the conversion of alkylaromatics to benzene, there is observed parasitic reactions of hydrocracking and/or steamcracking of the aromatic ring, which lead to undesirable gases such as $CO$, $CO_2$, $CH_4$, which reduce the hydrogen yield and the yield of aromatics.

OBJECTS OF THE INVENTION

Figure 1:
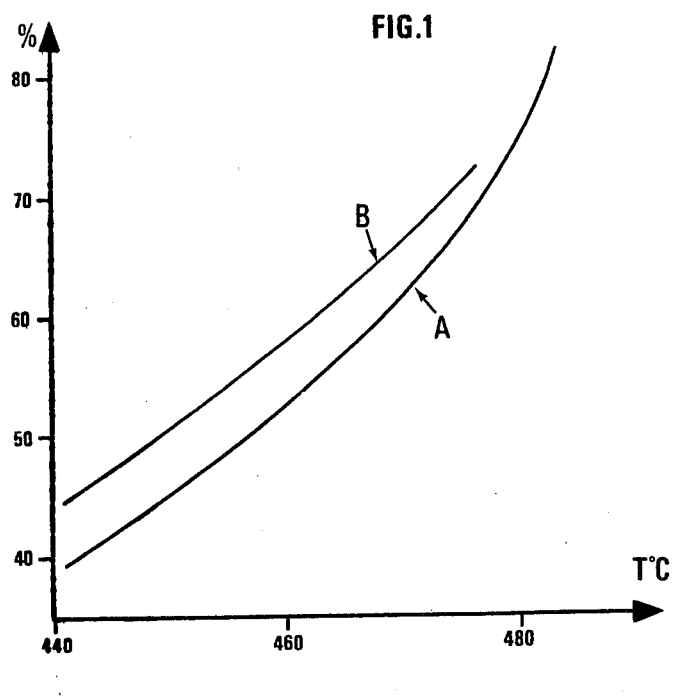
FIG. 1 is a plot of the molar percent conversion of the charge against test temperature.

The present invention has for object to obviate these major disadvantages and to provide a process where the yield of final product is increased by a selection of selective and stable catalysts.

DETAILED DISCUSSION

This object is achieved by preparing benzene and/or lower homologs thereof by dealkylation of alkylbenzenes (toluene, xylene, etc.) by steam conversion in the presence of specific catalysts.

The operation is generally conducted between 300° C. and 600° C., preferably between 350° C. and 550° C., under a pressure from 1 to 20 atmospheres and preferably from 3 to 10 atmospheres, with a LHSV ("Liquid Hourly Space Velocity") i.e. a liquid VVH (space velocity) comprised between 0.1 and 10 volumes of hydrocarbons per volume of catalyst and per hour, preferably from 1 to 5, with a ratio (by moles) $H_2O$/hydrocarbons between 1 and 20, preferably between 3 and 15.

In this process, there is obtained products of complete dealkylation like benzene as well as products of partial dealkylation such, for examples, as toluene from xylenes.

More precisely, the process provides for the production of benzene, toluene, xylenes, ethylbenzene and substantial amounts of hydrogen. According to this process it is, for example, possible to dealkylate toluene, xylenes, ethylbenzene, propylbenzene, methylbenzene or even hydrocarbons with condensed rings as naphthalene, phenanthrene, anthracene, etc. This is also true for mesitylene, pseudo cumene, hemimellitene; the process also provides for the aromatization followed with a dealkylation of such hydrocarbons as alkylcyclohexanes, alkyltetraline, alkyldecaline and alkyldihydroanthracene.

According to the process, aromatic nitrogen compounds may also be dealkylated, this is for example the case of pyridine, nitrogen being removed in the form of $NH_3$ or $N_2$.

The process is of a particular efficiency for dealkylating alkyl aromatic hydrocarbons obtained in the course of catalytic refoming reactions or reactions for the production of aromatic hydrocarbons (by aromizing).

The catalysts used according to the invention provide for high yields of dealkylated aromatics (for example, high benzene yields) with a simultaneous low rate of degradation of the aromatic ring. They provide for the production of a reaction gas of high hydrogen content (from 50 to 70% by volume of hydrogen) and of substantial value. They finally have a very good stability under the most severe operating conditions.

The specific catalysts used according to the invention comprise:

(a) a carrier, consisting essentially of alumina and, by weight:

(b) from 0.1 to 2% of at least one metal from group VIII of the periodic classification, having an atomic number of 44 or more, selected from the group consisting of ruthenium, rhodium, palladium, osmium, iridium and platinum, the preferred metal being rhodium;

(c) from 0.05 to 0.8% of rhenium;

(d) from 0.01 to 5% by weight of at least one alkali metal selected from the group consisting of lithium, sodium, potassium, rubidium and cesium.

Preferably, the catalaysts contain:

Either:

(a) An alumina carrier having a specific surface higher than 50 m² per gram and, preferably, higher than 80 m² per gram; and, by weight:

(b) from 0.1 to 0.5% of rhodium and 0.1 to 0.5% of at least one noble metal selected from the group consisting of platinum, palladium and ruthenium;

(c) from 0.1 to 0.8% of rhenium;

(d) from 0.5 to 5% by weight of at least one alkali metal selected from the group consisting of lithium, sodium, potassium, rubidium and cesium.

Or:

(a) an alumina carrier of a specific surface higher than 50 m² per gram and, preferably, higher than 80 m² per gram; and, by weight:

(b) from 0.25 to 0.70% of rhodium, (c) from 0.1 to 0.8% of rhenium;
(d) from 0.5 to 5% of at least one alkali metal selected from the group consisting of lithium, sodium, potassium, rubidium and cesium.

The catalyst carrier is preferably selected from the eta-cubic $\eta$, gamma cubic $\gamma_O$, gamma tetragonal $\gamma_T$, Chi $\chi$ cubic, Kappa-orthorhombic k, theta monoclinic $\theta$, deltaorthorhombic $\delta$ and rho-amorphous $\rho$ aluminas.

It exhibits a specific surface comprised between 50 and 400 m$^2$/g and preferably between 80 and 350 m$^2$/g and a total pore volume from 30 to 150 ml/100 g.

Any known method of manufacture of these catalysts may be used. The active elements will be deposited either simultaneously or separately on the carrier by impregnation, from aqueous solutions or from solutions in an appropriate solvent, of soluble salts of the above-mentioned active elements.

The impregnations may be conducted either in a dry state, by filling the pore volume of the carrier with an equal volume of the impregnation solution and then, after an optional maturation, by drying said carrier, or, with an excess of solution, by contacting the carrier with a volume of solution greater than the pore volume of said carrier and waiting for a sufficient time to have the metal ions contained in the solution fixed, for example by an exchange reaction, on the carrier.

As soluble salts of the above-mentioned active elements, there can be mentioned, as far as the noble metals of the group VIII, rhenium and alkali metals are concerned: the halides, nitrates, acetates, the basic carbonates, the formates, oxalates, citrates, the chlorometallic acids and their ammonium and amimes salts, the complexes containing at least one the above-mentioned metals with oxalic acid and the oxalates, citric acid and the citrates, tartaric acid and the tartarates, with other polyacids, alcohol acids, amino alcohols and their salts, the acetylacetonates. Rhenium is more particularly used as perrhenic acid or ammonium or potassium perrhenate.

For example, it is possible to impregnate the carrier with a solution containing at least one metal of the platinum family (group VIII) and then dry, for example between 100° and 250° C., for at least one hour, then optionally thermally activate (by roasting for at least one hour at a temperature from 300° to 600° C.), then impregnate with a solution containing a rhenium compound and optionally at least one alkali metal, dry and then optionally roast and/or reduce for at least one hour at about 300° to about 600° C. in the presence of a gas containing at least 10% of hydrogen, then finally optionally impregnate (if not previously made) with a solution containing at least one metal from group I$_A$(Li, Na, K, Rb, Cs) dry, rost and or reduce as above.

It is also possible, for example, to impregnate the carrier with a solution containing a rhenium compound and optionally at least one alkali metal and then to dry and roast between 200° and 350° C., for at least one hour and optionally to reduce the roasted carrier impregnated with the above-mentioned metals, for at least one hour between 300° and 600° C., then to impregnate it with a solution containing at least one metal of the platinum family (group VIII) and then to dry and activate and/or reduce as above-mentioned, then optionally impregnate (if not previously made) with a solution containing an alkali metal, dry and roast and/or reduce as above.

It is also possible, for example, to prepare a solution containing at least one metal of the platinum family (group VIII), at least one rhenium compound and at least one alkali metal, to impregnate the carrier with said solution and then to dry, roast and/or reduce it in the above-mentioned conditions.

Another process for preparing the catalyst consists of incorporating rodium in the form of chlororhodic acid, obtained from a hydrochloric solution of rhodium trichloride and simultaneously incorporating rhenium in the form of a hydrochloric acid solution of ammonium perrhenate, potassium perrhenate or perrhenic acid onto the alumina carrier. Both metals (rhodium, rhenium) being then probably in the form of anions, may be preferably exchanged on the alumina carrier so as to be homogeneously impregnated on said carrier. Any method, known in the art for obtaining said homogeneity, may be used. It is preferably that, after subsequent thermal treatments, the atomic ratio R=RH/Re, measured at any point of a catalyst particle, shaped as a ball or an extrudate, for example, in the internal volume of the particle, does not vary by more than ±0.1 R.

The rhodium and rhenium impregnated carrier is then drained, dried at 100°–200° C. for one hour or more, optionally roasted in the presence of air at a temperature from about 200° to about 400° C. for one hour or more, then impregnated with at least one compound of at least one alkali metal, dried and optionally roasted as before impregnation with said metals, then finally reduced with a gas containing at least 10% of hydrogen, preferably in a dry state, i.e. containing less than 0.5% by weight of steam, at a temperature from 300° to 700° C. and, preferably from 320° to 550° C., for at least one hour.

Preferably, before any contact with the alkylaromatic hydrocarbons subjected to dealkylation, a reduction treatment of the catalyst will be performed by passing a hydrogen stream at a temperature from 100° to 500° C.

The following non-limitative examples are given for illustrating purpose of the various aspects of the invention.

These examples concern the preparation of the catalysts according to the invention and the use thereof for dealkylating toluene in the presence of steam. The application to this particular hydrocarbon must not be considered as a limitation of the use of the catalysts. It has been selected only for testing the activity and the selectivity of the catalyst in a dealkylation operation, in the same manner as normal heptane is selected for testing the properties of the catalyst in reforming reactions or ethylbenzene for the aromatic hydrocarbon isomerization catalysts. As above mentioned, the alkylaromatic charges may be very diverse.

The preparation of the catalysts A to G will be first described, the catalysts B and F forming no part of the invention.

EXAMPLE 1

A $\gamma_C$ alumina carrier of the trade, consisting of balls of a diameter from 1.6 to 2.5 millimeters, having a specific surface of 210 m$^2$/g and a pore volume of 63 ml per 100 g, previously stoved at 70° C. in steam saturated atmosphere, is impregnated as follows:

1000 g of dry carrier, stoved at 70° C., are contacted with 1500 ml of a solution containing 5.1 g of rhodium in the form of hydrated rhodium trichloride and 40 ml of pure hydrochloric acid at the grade required for analysis (d=1.19). After exhaustion of the solution, it is observed that rhodium is distributed homogeneously in the balls of carrier. After draining, a drying step is performed at 100° C. for one hour and then at 200° C. for 2 hours and then a roasting step is performed for 1 hour at 350° C. The catalyst is then contacted with 1400 ml of a solution containing 9.4 of ammonium perrhenate and 20 ml of hydrochloric acid. After exhaustion of this solution, drying, draining at 100° C. for one hour and then at 200° C. for 2 hours, the resulting product is roasted at 290° C. for 5 hours in the presence of air.

The catalyst is then impregnated in dry state with 560 ml of a solution containing 10.2 g of potassium as nitrate, dried at 100° C. for one hour, then at 200° C. for 5 hours, and directly reduced with dry hydrogen at 300° C. for 30 minutes and then 500° C. for one hour. The obtained catalyst A contains by weight 0.5% of rhodium, 0.6% of rhenium and 1% of potassium.

EXAMPLE 2 (comparative)

The preparation of example 1 is reproduced up to the roasting step inclusive performed at 350° C. for one hour (after impregnation with rhodium). Then the product is impregnated in dry state with 10.2 g of potassium, dried and reduced as in example 1.

There is obtained cayalyst B which contains by weight 0.5% of rhodium and 1% of potassium. This catalyst does not contain rhenium.

EXAMPLE 3

In this example the catalyst comprises an alumina carrier, as available on the trade, consisting of extrudates having a diameter of 1.2 mm, a length from 5 to 7 mm, a specific surface of 250 m$^2$/g and a total pore volume of 54 ml/100 g, previously moistened by stoving at 70° C. (steam pressure=saturating pressure).

1000 g of this carrier are impregnated by immersion into 1300 ml of a solution containing 3.6 g. of rhodium (as trichloride), 4.2 g of palladium (as chloride) and 44 ml of pure hydrochloric acid at the grade required for analysis (d=1.19). After exhaustion of the solution it is observed that palladium and rhodium are homogeneously distributed in the balls of the carrier. After draining, the carrier, impregnated at 150° C. fo 5 hours, is dried and then contacted with 1300 ml of a solution containing 7.4 g of perrhenic acid and 20 ml of hydrochloric acid. After exhaustion of the solution and draining, drying is performed for 1 hour at 100° C. and for 5 hours at 160° C., and it is followed with a roasting step at 300° C., for 3 hours, in the presence of air.

The catalyst is finally impregnated in a dry state with 510 ml of a solution containing 11.6 g of potassium in the form of carbonate, dried at 130° C. for 10 hours, activated at 300° C. for 2 hours, and finally reduced with dry hydrogen at 300° C. for 50 minutes, and then at 480° C. for 1 hour. There is obtained a catalyst C which contains by weight 0.35% of rhodium, 0.41% of palladium, 0.53% of rhenium, and 1.1% of potassium.

EXAMPLE 4

The preparation of example 3 is repeated, except that the 4.2 g of palladium are replaced with 4.6 g of platinum in the form of chloroplatinic acid. The other steps of the preparation are unchange. There is obtained a catalyst D which contains by weight 0.35% of rhodium, 0.44% of platinum, 0.51% of rhenium and 1.1% of potassium.

EXAMPLE 5

1000 g of the carrier described in example 1, previously subjected to moistening as above-mentioned, are contacted with 1400 ml of a solution containing 8.3 g of ruthenium (as trichloride), 2.6 g of rhodium, as trichloride, 50 ml of pure hydrochloric acid at the grade required for analysis, 300 ml of ethanol and 50 g of citric acid monohydrate. After exhaustion of the solution, it is observed that ruthenium and rhodium are distributed homogeneously within the balls of the carrier. After draining and drying, at 130° C., for 10 hours, roasting is performed at 350° C. for 3 hours in the presence of air.

The catalyst is then placed in a pill shaper, and impregnated in a dry state with 600 ml of a solution containing 6.3 g of rhenium as ammonium perrhenate, 15.3 g of potassium as nitrate and 50 g of citric acid monohydrate. After 4 hours of maturation in air, the catalyst is dried at 130° C. for 10 hours, roasted in air at 300° C. for 4 hours, then reduced in the presence of dry hydrogen at 200° C. for 30 minutes, at 300° C. for 30 minutes and at 490° C. for 90 minutes. There is obtained catalyst E which contains, by weight, 0.8% of ruthenium, 0.23% of rhodium, 0.6% of rhenium and 1.48% of potassium.

EXAMPLE 6 comparative)

The preparation of example 5 is reproduced without adding rheunium. The dry impregnation solution used in the second step of preparation, then contains only potassium.

There is obtained catalyst F which contains, by weight, 0.8% of ruthenium, 0.23% of rhodium and 1.50% of potassium.

EXAMPLE 7

100 g of a $\gamma_C$ alumina carrier, available on the trade, consisting of balls having a diameter from 1.6 to 2.5 mm, a specific surface of 220 m$^2$/g, a pore volume of 60 ml per 100 g, previously stoved at 70° C. in steam saturated atmosphere, are contacted with 1600 ml of a solution containing 5.6 g of rhodium as trichloride, 8.5 g of ammonium perrhenate and 38 ml of pure hydrochloric acid at the grade required for analysis (d=1.19).

After exhaustion of the solution, it is observed that rhodium and rhenium are homogeneously distributed within the carrier. The latter is dried at 120° C. for 3 hours and then at 260° C. for 2 hours, then impregnated in dry state in a pill shaper, by means of 500 ml of a solution containing 10.5 g of potassium as carbonate. The catalyst is finally dried at 100° C. for 1 hour, at 200° C. for 3 hours, then reduced in a dry hydrogen stream at 300° C. for 30 minutes and then at 500° C. for one hour. There is obtained catalyst G which contains, by weigh, 0.54% of rhodium, 0.56% of rhenium and 1% of potassium.

EXAMPLE 8

In this example, the performances, in a standard test of toluene dealkylation, are compared for catalysts A and B.

The test conditions are as follows:
charge:
   toluene 98.2% (by weight)
   xylenes 1.8% (by weight)
space velocity (L.H.S.V.)=2 volumes of charge per volume of catalyst and per hour;
water ratio: H$_2$O/toluene=6 mole/mole
pressure: 7 relative atmospheres catalyst amount 750 g (=1 liter).

The molar conversion of the charge is defined as follows:

Conversion =
$$\frac{\text{toluene input} + \text{xylenes input} - (\text{toluene output} + \text{xylenes output})}{\text{toluene input} + \text{xylenes intput}}$$

The selectivity of the reaction is defined as follows:

$$\text{Selectivity} = \frac{\text{formed benzene}}{\text{converted toluene and xylenes}}$$

The benzene yield is equal to the product of the conversion by the selectivity.

Figure 2:
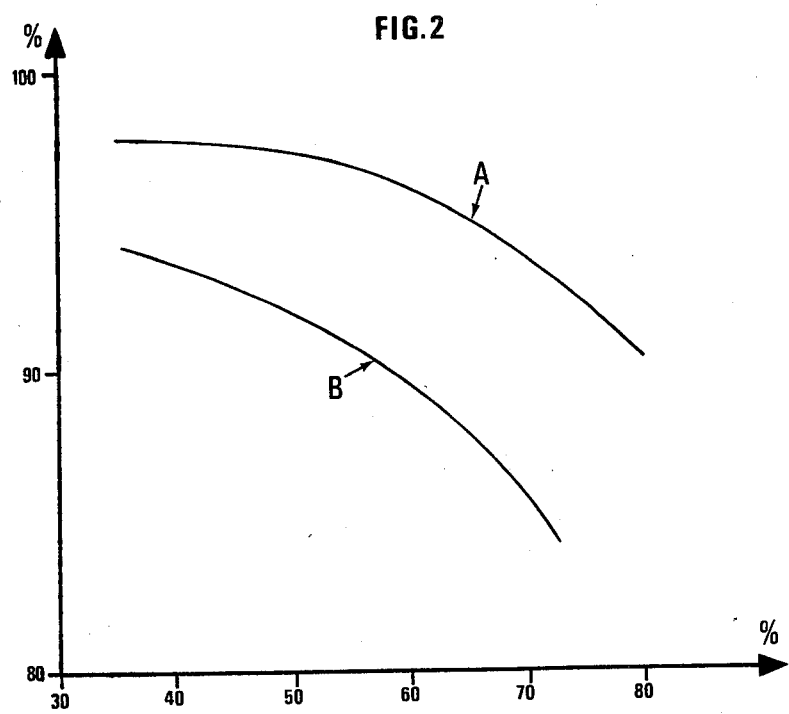
FIG. 2 is a plot of the molar percent conversion of the charge against selectively of conversion to benzene. of the charge against selectivity of conversion to benzene.

The performances of the catalysts A and B are indicated on FIGS. 1 and 2; FIG. 1 gives for each of catalysts A and B, the obtained molar conversion with respect to the charge, in relation with the test temperature; FIG. 2 gives, for each catalyst A and B, as abscissa, the molar conversion of the charge and, as ordinate, the obtained selectivity to benzene.

With each of catalysts A and B, the operation is first conducted for 50 hours at 460° C. Then, with each of catalysts A and B, several tests of 2 hours each are performed, at different temperatures. For each test, there is determined the conversion, the selectivity and the benzene yield. The curve showing the selectivity in relation with the conversion rate makes it possible to compare the two catalysts at iso-conversion. It is apparent that the catalyst used according to the invention (catalyst A), for the same conversion, gives 4 to 8 additional points of selectivity, according to the temperature, as compared with the catalyst B, which does not contain rhenium.

EXAMPLE 9

This example describes, with the charge and in the operating conditions of example 8, the performances of the catalysts of examples 1 to 7. The catalysts B and F form no part of the invention. The comparison between catalysts A and B on the one hand, and E and F, on the other hand, confirms the superiority of the catalysts used according to the invention. (Table I).

least one metal from group VIII, selected from ruthenium, rhodium, palladium, osmium, iridium and platinum, from 0.05 to 0.8% of rhenium and from 0.01 to 5% of at least one alkali metal selected from lithium, sodium, potassium, rubidium and cesium.

2. A process according to claim 1 wherein the catalyst contains, by weight, from 0.1 to 0.5% of rhodium, from 0.1 to 0.5% of at least one metal selected from the group consisting of platinum, palladium and ruthenium, from 0.1 to 0.8% of rhenium, from 0.5 to 5% of at least one alkali metal selected from lithium, sodium, potassium, rubidium and cesium, and includes an alumina carrier having a specific surface higher than 80 m² per gram.

3. A process according to claim 1, wherein the catalyst contains, be weight, from 0.25 to 0.7% of rhodium, from 0.1 to 0.8% of rhenium, from 0.5 to 5% of at least one alkali metal selected from the group consisting of lithium, sodium, potassium, rubidium and cesium, and includes an alumina carrier having a specific surface higher than 80 m² per gram.

4. A process according to claim 1 wherein, R being the atomic ratio Rh/Re in the catalyst, said catalyst consisting of balls or extrudates, the atomic ratio R, from one ball to another or from one extrudate to another and at any point of the internal volume of a ball or an extrudate, remains within the range of R±0.1 R (by weight).

5. A process according to claim 1, wherein the catalyst has been produced as follows: an alumina carrier is impregnated with rhodium and rhenium, then dried between about 100 and 200° C. for at least one hour, then roasted in the presence of air between about 200 and about 400° C. for at least one hour, then impregnated with at least one alkali metal, dried and then roasted at a temperature from about 200 to about 400° C. for at least one hour, then finally reduced in the presence of a gas containing at least 10% of hydrogen, between about 300° and about 700° C. for at least one hour, said gas containing less than 0.5% by weight of steam.

6. A process according to claim 1, as applied to the dealkylation of toluene to benzene.

7. A process according to claim 1, as applied to the

TABLE 1

| CATA-LYST | ACTIVE ELEMENTS (% b.w.) | T °C. | CONVER-* SION of CHARGE | BENZENE* SELECTI- VITY | BENZENE* YIELD | COMPOSITION OF THE PRODUCED GAS* | | | | |
|---|---|---|---|---|---|---|---|---|---|---|
| | | | | | | H₂ | CO₂ | CO | CH₄ | C₂H₆ |
| A | 0.5 Rh; 0.6 Re; 1 k | 470 | 61 | 95.8 | 58.4 | 62 | 23 | 0.9 | 13.7 | 0.4 |
| B | 0.5 Rh; 1 K | 464 | 61 | 89.2 | 54.4 | 58 | 28 | 1.4 | 12 | 0.6 |
| C | 0.35 Rh; 0.41 Pd; 0.53 Re; 1.1 K | 485 | 52 | 95.1 | 49.4 | 60.3 | 24 | 2.1 | 13 | 0.6 |
| D | 0.35 Rh; 0.44 Pt; 0.51 Re; 1.1 K | 490 | 56.8 | 94.5 | 53.7 | 59.2 | 26 | 1.6 | 12.9 | 0.3 |
| E | 0.80 Ru; 0.23 Rh; 0.6 Re; 1.48 K | 480 | 70 | 92.1 | 64.5 | 64.5 | 24 | 1.5 | 9.6 | 0.4 |
| F | 0.80 Ru; 0.23 Rh; 1.5 K | 474 | 70 | 83.2 | 58.2 | 55.5 | 25 | 1.2 | 17.6 | 0.7 |
| G | 0.54 Rh; 0.56 Re; 1 K | 472 | 71.2 | 95.0 | 67.6 | 66.9 | 22.1 | 2.5 | 8 | 0.5 |

* = % by mole

What we claim is:

1. A process for steam-dealkylating a charge containing at least one alkylaromatic hydrocarbon, in the presence of a catalyst containing an alumina carrier and, by weight with respect to the catalyst, from 0.1 to 2% of at least one alkylaromatic hydrocarbons issued from the effluents of catalytic reforming or from an aromatic hydrocarbon production unit.